US010925779B2

United States Patent
Matsumiya et al.

(10) Patent No.: US 10,925,779 B2
(45) Date of Patent: Feb. 23, 2021

(54) DISPOSABLE UNDERGARMENT AND METHOD FOR MANUFACTURING DISPOSABLE UNDERGARMENT

(71) Applicant: KOYO CORPORATION, Kanagawa (JP)

(72) Inventors: Munetada Matsumiya, Kanagawa (JP); Atsuko Shirai, Kanagawa (JP)

(73) Assignee: KOYO CORPORATION, Kanagawa (JP)

( * ) Notice: Subject to any disclaimer, the term of this patent is extended or adjusted under 35 U.S.C. 154(b) by 93 days.

(21) Appl. No.: 15/855,586

(22) Filed: Dec. 27, 2017

(65) Prior Publication Data

US 2018/0125728 A1 May 10, 2018

Related U.S. Application Data

(63) Continuation of application No. PCT/JP2017/013042, filed on Mar. 29, 2017.

(30) Foreign Application Priority Data

Mar. 31, 2016 (JP) .............................. JP2016-071433

(51) Int. Cl.
*A61F 13/496* (2006.01)
*A61F 13/15* (2006.01)
(Continued)

(52) U.S. Cl.
CPC .......... *A61F 13/4963* (2013.01); *A61F 13/15* (2013.01); *A61F 13/15585* (2013.01);
(Continued)

(58) Field of Classification Search
CPC .... A61F 13/15; A61F 13/49; A61F 13/49058; A61F 13/4906; A61F 2013/49068;
(Continued)

(56) References Cited

U.S. PATENT DOCUMENTS 6,979,380 B2 * 12/2005 Thorson ............ A61F 13/15699
156/164
9,144,523 B2 9/2015 Takahashi et al.
(Continued)

FOREIGN PATENT DOCUMENTS

JP 2002-272781 A 9/2002
JP 3862510 B2 12/2006
(Continued)

OTHER PUBLICATIONS

"Match." Merriam-Webster.com Dictionary, Merriam-Webster, https://www.merriam-webster.com/dictionary/match. Accessed Jul. 31, 2020.*
(Continued)

*Primary Examiner* — Michele M Kidwell
(74) *Attorney, Agent, or Firm* — Michael Best & Friedrich LLP

(57) ABSTRACT

A crotch member of a disposable under garment is joined to central portions of a symmetrical ventral member and a symmetrical dorsal member. A crotch side edge of the ventral member includes a recessed line symmetrically recessed toward a waist side edge between a center line and left and right end portions of the ventral member. The recessed line includes bottom portions each closest to the waist side edge located at a position closer to the left and right end portions than the center line. A crotch side edge of the dorsal member include a protruding line symmetrically protruding away from a waist side edge between a centerline and left and right end portions of the dorsal member. The protruding line includes top portions farthest away from the waist side edge located at a position closer to the centerline than the left and right end portions.

5 Claims, 10 Drawing Sheets

(51) Int. Cl.
  *A61F 13/49*  (2006.01)
  *B32B 37/20*  (2006.01)
  *A61F 13/72*  (2006.01)
  *B32B 37/12*  (2006.01)
  *B32B 38/00*  (2006.01)

(52) U.S. Cl.
  CPC .. *A61F 13/15699* (2013.01); *A61F 13/15723* (2013.01); *A61F 13/49* (2013.01); *A61F 13/49012* (2013.01); *A61F 13/49017* (2013.01); *A61F 13/49061* (2013.01); *A61F 13/72* (2013.01); *B32B 37/12* (2013.01); *B32B 37/206* (2013.01); *A61F 2013/49092* (2013.01); *B32B 38/0004* (2013.01); *B32B 2555/02* (2013.01)

(58) Field of Classification Search
  CPC ............ A61F 13/4963; A61F 13/49061; A61F 13/15585; A61F 13/15699; A61F 13/15723; A61F 13/49012; A61F 13/49017; A61F 13/72; B32B 2555/02
  See application file for complete search history.

(56) References Cited

U.S. PATENT DOCUMENTS

| 2002/0129888 | A1  | 9/2002 | Otsubo et al. |
| 2004/0060649 | A1* | 4/2004 | Van Gompel ......... A61F 13/539 156/258 |
| 2005/0010188 | A1  | 1/2005 | Glaug et al. |
| 2016/0235600 | A1* | 8/2016 | Suzuki ............. A61F 13/15593 |

FOREIGN PATENT DOCUMENTS

| JP | 2009-273922 A | 11/2009 |
| JP | 2010-104415 A | 5/2010 |
| JP | 2012-100587 A | 5/2012 |
| JP | 5848502 B2 | 1/2016 |
| WO | WO-2016/076223 A1 | 5/2016 |
| WO | WO-2016/076224 A1 | 5/2016 |

OTHER PUBLICATIONS

International Search Report issued in Application No. PCT/JP2017/013042, dated Jun. 13, 2017.

* cited by examiner

DISPOSABLE UNDERGARMENT AND METHOD FOR MANUFACTURING DISPOSABLE UNDERGARMENT

RELATED APPLICATION

This is a continuation of International Application No. PCT/JP2017/013042 filed on Mar. 29, 2017 claiming priority based on Japanese Patent Application No. 2016-071433 filed on Mar. 31, 2016, the contents of these applications of which, including the specifications, the claims and the drawings, are incorporated herein by reference in their entirety.

TECHNICAL FIELD

The present invention relates to a disposable undergarment, in particular, a disposable pant-type diaper or an absorbent pad holder, and a method for manufacturing a disposable undergarment.

BACKGROUND ART

A pant-type disposable undergarment includes a waist opening at the top and left and right leg openings at the bottom. A known method for continuously manufacturing such a pant-type disposable undergarment forms the leg openings by cutting out a web, that is, a material of a disposable undergarment, leading to generation of a waste material. Methods for continuously manufacturing a pant-type disposable undergarments with reduced waste of material have been proposed in several Patent Literatures.

In the method for manufacturing a pant-type disposable diaper disclosed in JP 3862510 B2, a pair of parallel leg-surrounding elastic members is joined to a stream of a sheet-like web, in a sine curve shape along the web center line. The web is cut into the sine curve shape between the pair of leg-surrounding elastic members and divided into two half-webs. The two half-webs are spaced apart in a direction orthogonal to a web flow direction. An absorbent pad member is joined to the two half-webs alternately in opposite orientations of the ventral and dorsal orientations in every half cycle in the web flow direction. The pad member is folded to allow the two half-webs to be overlaid with each other and to be joined in every half cycle in the flow direction. Both the half-webs are cut at every neighboring portion of the joint, thereby forming a disposable undergarment. Such a manufacturing method in Japanese patent Publication JP 3862510 B2 continuously manufactures the pant-type disposable undergarment with the ventral and dorsal orientations alternately reversed, and thus, takes time and effort to align the orientation of the disposable undergarment. In addition, the pant-type disposable undergarment in JP 3862510 B2 has same shapes of the entire crotch side edges of both the ventral member and the dorsal member formed by cutting the sheet member into two, making it difficult to realize both the shape appropriate for the ventral member and the shape appropriate for the dorsal member. In particular, in the pant-type disposable undergarment in JP 3862510 B2, the distance between the crotch side edge and the waist side edge of the ventral member decreases from the left and right end portions toward the center, leading to a shape different from the usual pant-type undergarment and unfamiliar with a wearer.

In the manufacturing method of the pant-type disposable undergarment disclosed in Japanese Patent Publication JP 5848502 B2, a pair of parallel leg-surrounding elastic members extending in a meandering manner in the flow direction is arranged on a first sheet along the neighborhood of the center line in a width direction, and a second sheet is overlaid thereon and joined to form a sheet member. The sheet member is cut between the pair of leg-surrounding elastic members extending in a meandering manner along the neighborhood of the center line and divided into a ventral sheet member and a dorsal sheet member. The ventral sheet member and the dorsal sheet member are spaced apart in a direction orthogonal to the flow direction. The absorbent body is joined to the ventral sheet member and the dorsal sheet member in every cycle in the flow direction. The absorbent body is folded, and the ventral sheet member and the dorsal sheet member are overlaid with each other and joined in every cycle in the flow direction and are cut at every neighboring portion of the joint. In such a manufacturing method of JP 5848502 B2, the pant-type disposable undergarment is continuously manufactured in a same orientation. In the ventral sheet member and the dorsal sheet member, however, the cut edge between the absorbent bodies joined to both sides meanders with respect to the flow direction in every cycle and the leg-surrounding elastic member along the cut edge also meanders. Therefore, when overlaying and joining the ventral sheet member and the dorsal sheet member to which the absorbent body is joined, the ventral sheet member and the dorsal sheet member might be joined in a state where positions of end portions on the cut edge side of the joint are shifted by contraction of the elastic member, leading to a problem of generating wrinkles in the joint. In addition, the pant-type disposable undergarment in JP 5848502 B2 has same shapes of the entire crotch side edges of the ventral member and the dorsal member formed by cutting the sheet member into two, making it difficult to realize both the shape appropriate for the ventral member and the shape appropriate for the dorsal member.

The method for manufacturing a pant-type disposable undergarment disclosed in WO 2005/007051 A1 is substantially the same as the method in JP 5848502 B2, except for a difference that a pair of parallel leg-surrounding elastic members extends in a meandering manner along the flow direction of the sheet member at a position deviated to one side from the center line in the width direction of the sheet member. The pant-type disposable undergarment manufactured with the method of WO 2005/007051 A1 has same shapes of the entire crotch side edges of both the ventral member and the dorsal member formed by cutting the sheet member into two, making it difficult to realize both the shape appropriate for the ventral member and the shape appropriate for the dorsal member.

SUMMARY OF INVENTION

A disposable undergarment of this application includes a ventral member, a dorsal member including left and right end portions respectively joined to left and right end portions of the ventral member and a crotch member joined to both central portions of the ventral member and the dorsal member. Each of the ventral member and the dorsal member includes an elastic body that is expandable and shrinkable at least in a left-right direction. A left half of a crotch side edge of the ventral member has a same shape as a shape of a right half of a crotch side edge of the dorsal member. A right half of the crotch side edge of the ventral member has a same shape as a shape of a left half of the crotch side edge of the dorsal member. The left half and the right half of the crotch side edge of the ventral member are symmetrical about a center line of the ventral member. The left half and the right half of the crotch side edge of the ventral member respectively include a left recessed line and a right recessed line recessed in a direction toward a waist side edge of the ventral member, between the centerline of the ventral member and the left and right end portions. Each of the left recessed line and the right recessed line includes a bottom portion closest to the waist side edge of the ventral member, being located at a position excluding the center line and the left and right end portions, located at a position closer to the left and right end portions than the center line. The left half and the right half of the crotch side edge of the dorsal member are symmetrical about a center line of the dorsal member. The left half and the right half of the crotch side edge of the dorsal member respectively include a left protruding line and a right protruding line protruding in a direction away from a waist side edge of the dorsal member, between the center line of the dorsal member and the left and right end portions. Each of the left protruding line and the right protruding line includes a top portion farthest away from the waist side edge of the dorsal member, being located at a position excluding the center line and the left and right end portions, located at a position closer to the center line than the left and right end portions.

In a method for manufacturing a disposable undergarment according to the present invention, a laminated web is formed by joining an inner web and an outer web with each other with an expandable and shrinkable elastic body to be expanded at least in the web flow direction sandwiched between the webs. By cutting the laminated web along a cutting line continuous in the web flow direction with the crotch side edge of one of the ventral member and the dorsal member of the disposable undergarment as one cycle, the laminated web is divided into a half-web formed of continuous ventral member and a half-web formed of continuous dorsal member. One of the half-web formed of continuous ventral member or the half-web formed of continuous dorsal member is moved in a web width direction while shifted by half cycle in the web flow direction so as to allow the ventral member and the dorsal member to be spaced apart from each other and to face each other in every cycle. Each of the crotch members is joined to the ventral member and the dorsal member in every cycle of both the half-webs. Both the webs are overlaid with each other in a state where each of the crotch members is folded. The ventral member and the dorsal member in each of cycles are joined with each other at each of the left and right end portions. A disposable undergarment is formed by cutting the joined ventral member and the dorsal member in every cycle.

Further details, features, and advantages of the present invention will become apparent from the following description with reference to the drawings of preferred exemplary embodiments.

DESCRIPTION OF EMBODIMENTS

Figure 1:
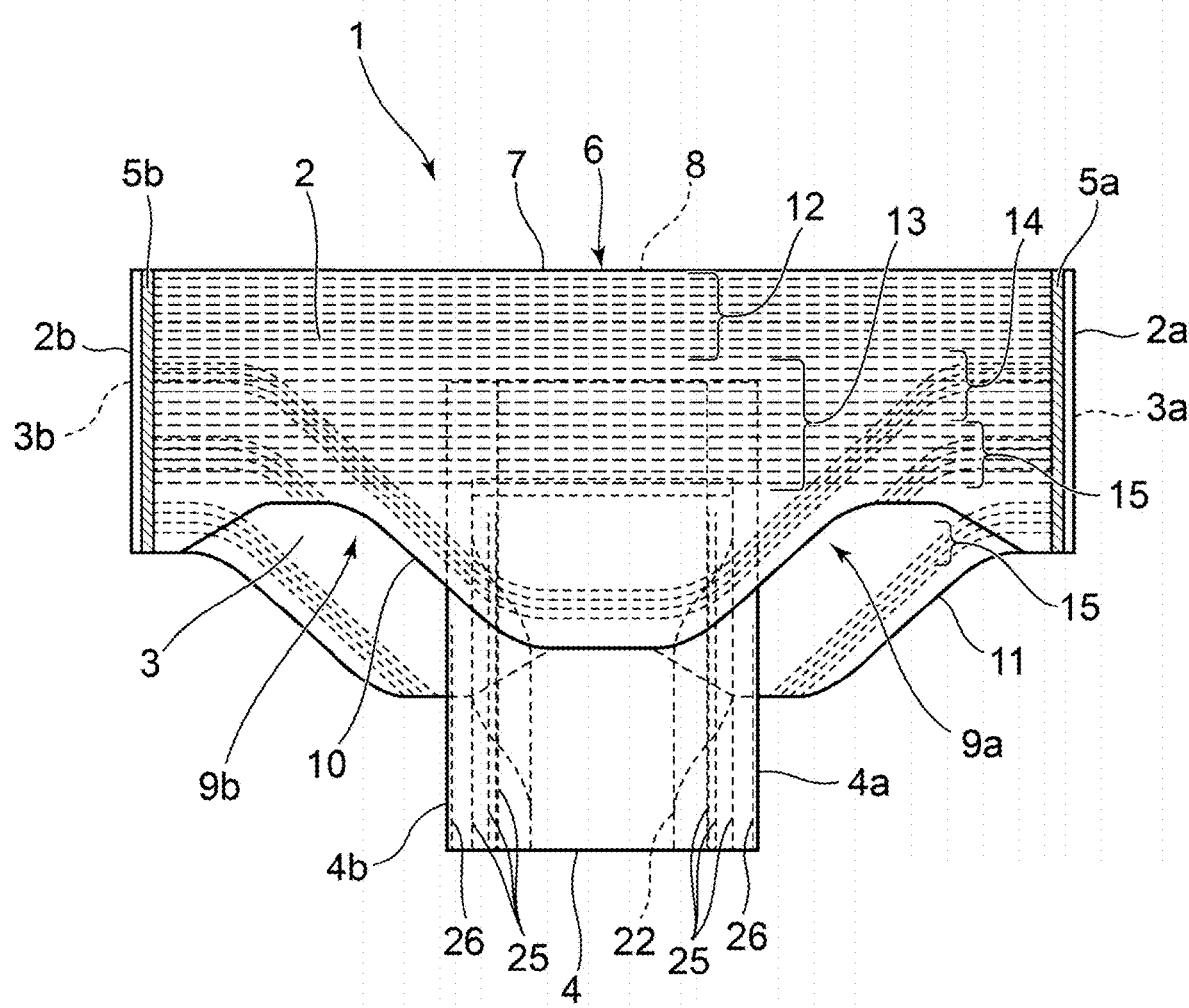
FIG. 1 is a front view of a disposable undergarment according to one embodiment of the present invention.
Figure 2:
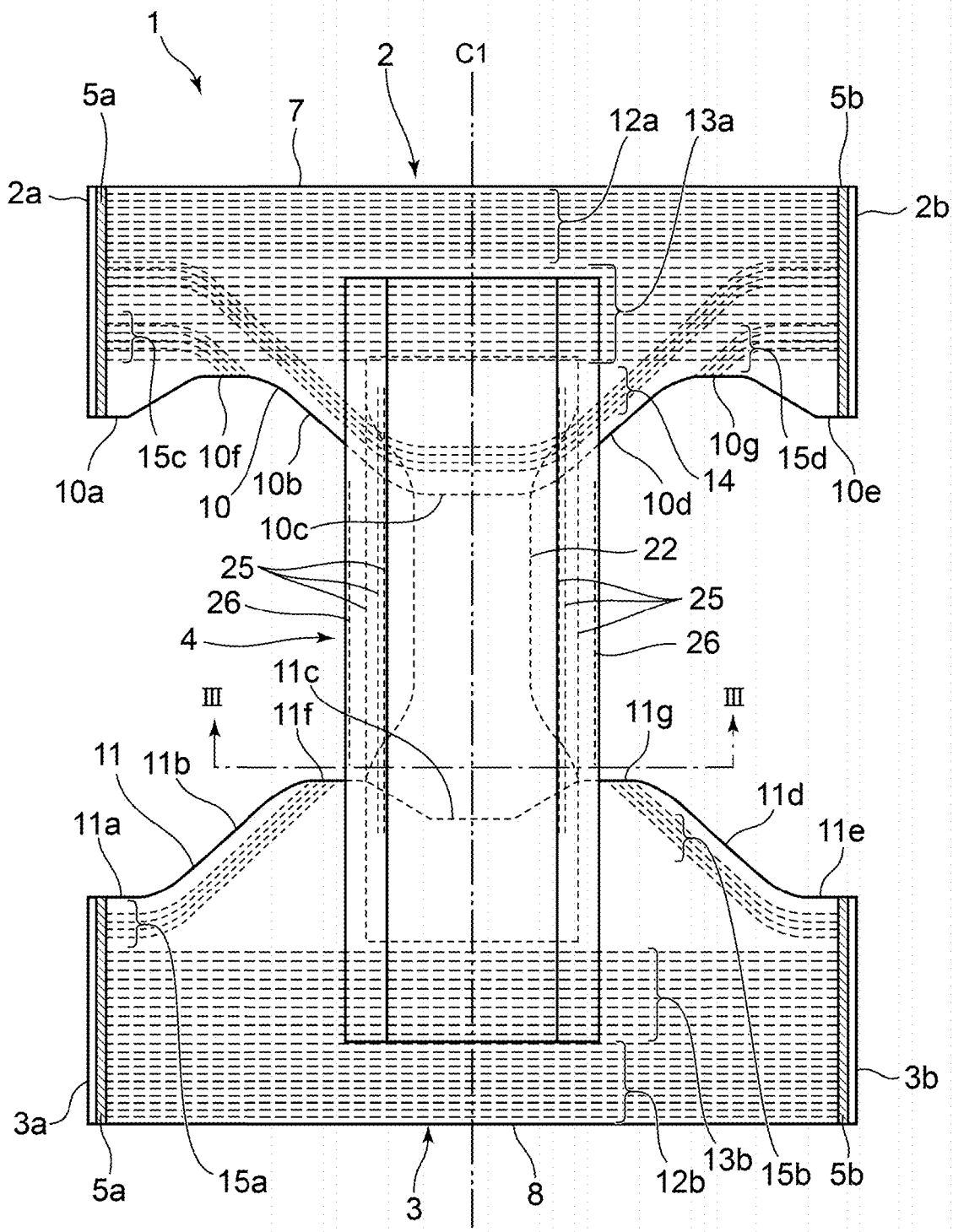
FIG. 2 is an exploded view of the disposable undergarment illustrated in FIG. 1.

A disposable undergarment of one exemplary embodiment of the present invention will be described with reference to the drawings. FIG. 1 is a front view of a disposable undergarment of one embodiment of the present invention. FIG. 2 is an exploded view of the disposable undergarment illustrated in FIG. 1. The disposable undergarment illustrated in FIGS. 1 and 2 illustrates a state where the elastic body is expanded without being contracted. As illustrated in FIG. 1 or 2, a disposable undergarment 1 according to the present embodiment is a pant-type disposable diaper. The disposable undergarment 1 includes a ventral member 2 positioned on a front side of a wearer's torso, a dorsal member 3 positioned on a back side of the wearer's torso, and a crotch member 4 joined to a central portion on an inner surface side of the ventral member 2 and to a central portion of an inner surface side of the dorsal member 3 and located at the crotch of the wearer.

The ventral member 2 and the dorsal member 3 are formed by overlaying an inner sheet positioned on a skin side of the wearer and an outer sheet positioned on a clothing side of the wearer sandwiching elastic bodies 12, 13, 14, and 15 between the sheets, and by joining the sheets. The material of the inner sheet and the outer sheet is a nonwoven fabric, but not limited to this, and it is allowable to use a resin film, a tissue, a stretchable sheet, a laminate thereof, or a sheet member formed by appropriately joining these together. Furthermore, the inner sheet and the outer sheet may also be formed by folding one sheet.

The pant-type disposable undergarment 1 is formed by bending the crotch member 4 joined to the ventral member 2 and the dorsal member 3 so as to allow the ventral member 2 and the dorsal member 3 to be overlaid with each other, and joining the left and right end portions of both the members 2 and 3. More specifically, a left joint 5a is formed along left end portions 2a and 3a of the ventral member 2 and the dorsal member 3, respectively, and a right joint 5b is formed along right end portions 2b and 3b of the ventral member 2 and the dorsal member 3, respectively. The left and right joints 5a and 5b may be formed by an adhesive such as a hot melt adhesive or by various sealing methods such as heat sealing and ultrasonic sealing.

A waist opening 6 of the disposable undergarment 1 is formed by being encircled by a waist side edge 7 at an upper end of the ventral member 2 and by a waist side edge 8 at an upper end of the dorsal member 3. The left leg opening 9a is formed by being encircled by a crotch side edge 10 at a lower end of the ventral member 2, a crotch side edge 11 at a lower end of the dorsal member 3, and a left side edge 4a of the crotch member 4. The right leg opening 9b is formed by being encircled by the crotch side edge 10 of the ventral member 2, the crotch end edge 11 of the dorsal member 3, and a right side edge 4b of the crotch member 4.

As illustrated in FIG. 1 or 2, in a state where the ventral member 2 and the dorsal member 3 are expanded, the waist side edge 7 of the ventral member 2 and the waist side edge 8 of the dorsal member 3 have linear shapes and an equal length. The left and right end portions 2a and 2b of the ventral member 2 have linear shapes perpendicular to the waist side edge 7. The left and right end portions 3a and 3b of the dorsal member 3 have linear shapes perpendicular to the waist side edge 8. The lengths of the left and right end portions 2a and 2b of the ventral member 2 are equal to the lengths of the left and right end portions 3a and 3b of the dorsal member 3, respectively. Each of the crotch side edge 10 of the ventral member 2 and the crotch side edge 11 of the dorsal member 3 has a symmetrical shape about a center line C1 having a common left-right widths on the ventral member 2 and the dorsal member 3.

As illustrated in FIG. 2, in a state where the ventral member 2 and the dorsal member 3 are separated and expanded, that is, in a state where the disposable undergarment 1 is developed, a left half and a right half of the crotch side edge 10 of the ventral member 2 are symmetrical about the centerline C1. The crotch side edge 10 includes a left end line 10a, a left recessed line 10b, an intermediate line 10c, a right recessed line 10d, and a right end line 10e. The left end line 10a, the intermediate line 10c, and the right end line 10e have linear shapes substantially parallel to the waist side edge 7. The intermediate line 10c is bisected by the center line C1. The left recessed line 10b is connected to the left end line 10a and the intermediate line 10c. The left recessed line 10b has a shape recessed in a direction toward the waist side edge 7. A bottom portion 10f of the left recessed line 10b is a portion closest to the waist side edge 7 and is located more toward the left end portion 2a than the center line C1 of the ventral member 2. The right recessed line 10d is connected to the right end line 10e and the intermediate line 10c. The right recessed line 10d has a shape recessed in a direction toward the waist side edge 7. A bottom portion 10g of the right recessed line 10d is a portion closest to the waist side edge 7 and is located more toward the right end portion 2b than the center line C1 of the ventral member 2.

As illustrated in FIG. 2, the left half and the right half of the crotch side edge 11 of the dorsal member 3 are symmetrical about the center line C1. The crotch side edge 11 includes a left end line 11a, a left protruding line 11b, an intermediate line 11c, a right protruding line 11d, and a right end line 11e. The left end line 11a, the intermediate line 11c, and the right end line 11e have a linear shape substantially parallel to the waist side edge 8. The intermediate line 11c is bisected by the center line C1. The left protruding line 11b is connected to the left end line 11a and the intermediate line 11c. The left protruding line 11b has a shape protruding in a direction away from the waist side edge 8. A top portion 11f of the left protruding line 11b is a portion farthest away from the waist side edge 8 and is located more toward the center line C1 than the left end portion 3a of the dorsal member 3. The right protruding line 11d is connected to the right end line 11e and the intermediate line 11c. The right protruding line 11d has a shape protruding in a direction away from the waist side edge 8. A top portion 11g of the right protruding line 11d is a portion farthest away from the waist side edge 8 and is located more toward the center line C1 than the right end portion 3b of the dorsal member 3.

As illustrated in FIG. 2, the shape of a left half of the crotch side edge 10 bisected at the center line C1 of the ventral member 2 is the same as the shape of the right half of the crotch side edge 11 bisected at the center line C1 of the dorsal member 3. The shapes of the left end line 10a, the left protruding line 10b, the bottom portion 10f, and the left half of the intermediate line 10c of the crotch side edge 10 are the same as the shapes of the right half of the intermediate line 11c, the right protruding line 11d, the top portion 11g, and the right end line 11e of the crotch side edge 11, respectively. In short, when the left half of the crotch side edge 10 of the ventral member 2 is moved in the left-right direction and in an approaching direction to abut the right half of the crotch side edge 11 of the dorsal member 3, the shapes of both portions match.

As illustrated in FIG. 2, the shape of a right half of the crotch side edge 10 bisected at the center line C1 of the ventral member 2 is the same as the shape of the left half of the crotch side edge 11 bisected at the center line C1 of the dorsal member 3. The shapes of the right end line 10e, the right protruding line 10d, the bottom portion 10g, and the right half of the intermediate line 10c of the crotch side edge 10 are the same as the shapes of the left half of the intermediate line 11c, the left protruding line 11b, the top portion 11f, and the left end line 11a of the crotch side edge 11, respectively. In short, when the right half of the crotch side edge 10 of the ventral member 2 is moved in the left-right direction and in an approaching direction to abut against the left half of the crotch side edge 11 of the dorsal member 3, the shapes of both portions match.

In the ventral member 2 of the disposable undergarment 1, the left and right bottom portions 10f and 10g having the shortest distance between the waist side edge 7 and the crotch side edge 10 are located at positions more toward the left and right end portions 2a and 2b, respectively, than the center line C1 of the ventral member 2. This configuration makes it possible to increase the left-right width of a downward protrusion between the left and right bottom portions 10f and 10g of the ventral member 2, leading to an increase in the left-right width of a region to cover the wearer's groin and periphery thereof on the ventral member 2. In this manner, the disposable undergarment 1 can form the ventral member 2 into an appropriate shape.

Furthermore, in the disposable undergarment 1, the distance between the waist side edge 7 and the crotch side edge 10 of the ventral member 2 is longer at a position of the center line C1 of the ventral member 2 than at the position of the left and right end portions 2a and 2b of the ventral member 2. This makes it possible to also increase a top-bottom length of the downward protrusion at the center of the ventral member 2. In this manner, the disposable undergarment 1 can realize an appropriate shape of the ventral member 2 with the increased left-right width and the top-bottom length of the region to cover the wearer's groin and periphery thereof.

The dorsal member 3 of the disposable undergarment 1 is configured such that the left and right protruding lines 11b and 11d continuous respectively to the left and right end lines 11a and 11e protrude in a direction away from the waist side edge 8, making it possible to increase the left-right width of the downward protrusion of the dorsal member 3. Moreover, in the dorsal member 3, the top portions 11f and 11g having the longest distance between the waist side edge 8 and the crotch side edge 11 are respectively located more toward the center line C1 than the left and right end portions 3a and 3b of the dorsal member 3. This configuration makes it possible to locate the top portions 11f and 11g of the downward protrusion of the dorsal member 3 near the central portion of the dorsal member 3 to which the crotch member 4 has been joined. The recessed shape of the intermediate line 11c of the dorsal member 3 would be no problem since the central portion of the dorsal member 3 is covered with the crotch member 4. In this manner, the disposable undergarment 1 makes it possible to realize an appropriate shape of the dorsal member 3 with the increased left-right width and the top-bottom length of the portion to cover the buttock of the wearer.

Furthermore, in the disposable undergarment 1, the crotch member 4 overlaps with a portion of the top portions 11f and 11g, which are portions respectively farthest away from the waist side edge 8 of the left and right protruding lines 11b and 11d of the crotch side edge 11 of the dorsal member 3. This configuration suppress generation of a recess in a boundary between the crotch member 4 and the dorsal member 3, making it possible to realize an appropriate shape of the dorsal member 3, capable of further enhancing prevention of leakage of wastes, or the like.

Furthermore, in the disposable undergarment 1 forms the depth of the recess from the top portions 11f and 11g of the crotch side edge 11 of the dorsal member 3 to the intermediate line 11c to be greatly smaller than a height of the protrusion from the left and right end portions 3a and 3b of the dorsal member 3 to the top portions 11f and 11g. This makes it possible to reduce the size of the recess in the central portion of the dorsal member 3 and achieve better appearance. Moreover, since the recess in the central portion of the dorsal member 3 is small, it is relatively easy to bond the crotch member 4 to the central portion of the dorsal member 3.

As illustrated in FIGS. 1 and 2, the ventral member 2 and the dorsal member 3 each includes waist-fitting elastic bodies 12a and 12b and body-fitting elastic bodies 13a and 13b configured to stretch and contract in the left-right direction. Moreover, the ventral member 2 includes a leg-fitting elastic body 14 and a portion of a leg-fitting elastic body 15. The dorsal member 3 includes a portion of the leg-fitting elastic body 15. With the presence of these elastic bodies, the ventral member 2 and the dorsal member 3 have regions that stretch and contract.

The waist-fitting elastic body 12a is arranged over substantially the entire region from the left end portion 2a to the right end portion 2b in the waist side edge 7 and adjacent regions of the ventral member 2, and is joined in an expanded state, to the ventral member 2. The waist-fitting elastic body 12b is arranged over substantially the entire region from the left end portion 3a to the right end portion 3b in the waist side edge 8 and adjacent regions of the dorsal member 3, and is joined in an expanded state, to the dorsal member 3. Although not illustrated, since the waist-fitting elastic bodies 12a and 12b are contracted in the disposable undergarment 1 that is placed at rest, waist gathers are formed in a region where the waist-fitting elastic bodies 12a and 12b of the ventral member 2 and the dorsal member 3 are joined. The waist gathers suitably allow the waist opening 6 of the disposable undergarment 1 to come in close contact with the wearer to prevent the falling down of the diaper 1 and the leakage of wastes, or the like, from the waist opening 6.

The body-fitting elastic body 13a is arranged over substantially the entire area from the left end portion 2a to the right end portion 2b, in the adjacent region on the crotch side edge 10 side from the region where the waist-fitting elastic body 12a of the ventral member 2 is joined, and is joined in an expanded state, to the ventral member 2. The body-fitting elastic body 13b is arranged over substantially the entire area from the left end portion 3a to the right end portion 3b in the adjacent region on the crotch side edge 11 side from the region where the waist-fitting elastic body 12b of the dorsal member 3 is joined, and is joined in an expanded state, to the dorsal member 3. Although not illustrated, since the body-fitting elastic bodies 13a and 13b are contracted in the disposable undergarment 1 that is placed at rest, body-fitting gathers are formed in a region where the body-fitting elastic bodies 13a and 13b of the ventral member 2 and the dorsal member 3 are joined. The body-fitting gathers suitably allow the ventral member 2 and the dorsal member 3 of the disposable undergarment 1 to come into close contact with the wearer, increases the fitness, and prevents leakage of wastes, or the like.

The leg-fitting elastic body 14 is arranged in a meandering manner so as to extend along the intermediate line 10c and the left and right recessed lines 10b and 10d of the crotch side edge 10 of the ventral member 2, rise diagonally away from the crotch side edge 10 from the front of the bottom portions 10f and 10g, and extend to the left and right end portions 2a and 2b of the ventral member 2 along the upper portion in the region of the body-fitting elastic body 13a, and is joined to the ventral member 2 in an expanded state. The leg-fitting elastic body 15 includes: a portion 15a extending along the left end line 11a and the left protruding line 11b of the crotch side edge 11 of the dorsal member 3 and intersecting the top portion 11f; a portion 15b extending along the right end line 11e and the right protruding line 11d of the crotch side edge 11 of the dorsal member 3 and intersecting the top portion 11g; and left and right portions 15c and 15d extending being spaced apart in parallel with each other below the leg-fitting elastic body 14 in the ventral member 2. Although not illustrated, since the leg-fitting elastic bodies 14 and 15 are contracted in the disposable undergarment 1 that is placed at rest, leg gathers are formed in the region where the leg-fitting elastic body 14 is joined around the crotch side edge 10 of the ventral member 2 and in the region where the leg-fitting elastic body 15 is joined around the crotch side edge 11 of the dorsal member 3. The leg gathers suitably allow the left and right leg openings 9a and 9b of the disposable undergarment 1 to come into close contact with the wearer, and prevents the leakage of wastes, or the like, from the leg openings 9a and 9b.

The waist-fitting elastic bodies 12a and 12b, the body-fitting elastic bodies 13a and 13b, and the leg-fitting elastic bodies 14 and 15 are formed with a group of a plurality of thread-like elastic bodies. Each of the thread-like elastic bodies is formed of a stretchable material such as natural rubber, polyurethane resin, and stretchable hot melt. The elastic bodies 12, 13, 14, and 15 are not limited to thread-like elastic bodies, but may be band-like elastic bodies or sheet-like elastic bodies. In addition, by forming the ventral member 2 and/or the dorsal member 3 as a whole with a material such as a stretchable sheet, the ventral member 2 and/or the dorsal member 3 may have stretchable regions. In the case of using a sheet-like elastic body or forming the entire ventral member 2 or the dorsal member 3 as a whole of a material such as a stretchable sheet, processing is performed so as to allow a desired tension to act in a direction similar to each of the elastic bodies 12, 13, 14, and 15.

In FIG. 2, the elastic bodies 12 and 13, and/or 14 arranged in a region of the ventral member 2 and/or the dorsal member 3 overlaid with the crotch member 4 may be processed to reduce the tension of the elastic body. This processing results in suppression of deformation or contraction of the crotch member 4 by the tension of the elastic body. As processing of reducing the tension of the elastic body, for example, it is possible to appropriately select, for example, finely dividing the elastic body with a large number of protrusions, a cutter blade or the like, finely heat sealing the elastic body, or the like.

As illustrated in FIG. 2, the crotch member 4 has a substantially rectangular shape, and the overlaid portion of the crotch member 4 and the ventral member 2 and the overlaid portion of the crotch member 4 and the dorsal member 3 are individually joined by an adhesive, or the like. Each of the end edges of the crotch member 4 in the longitudinal direction is located in the neighborhood of the boundary between the regions of the waist-fitting elastic bodies 12a and 12b of the ventral member 2 or the dorsal member 3 and the regions of the body-fitting elastic bodies 13a and 13b. Note that the shape of the crotch member 4 is not limited to a substantially rectangular shape, and may be a band-like shape in which both end edges in the longitudinal direction are curved. The position and the size of the portion overlaid and joined to the ventral member 2 or the dorsal member 3 of the crotch member 4 are not limited to those described above and may be appropriately changed in accordance with the size and shape of the disposable undergarment.

Figure 3:
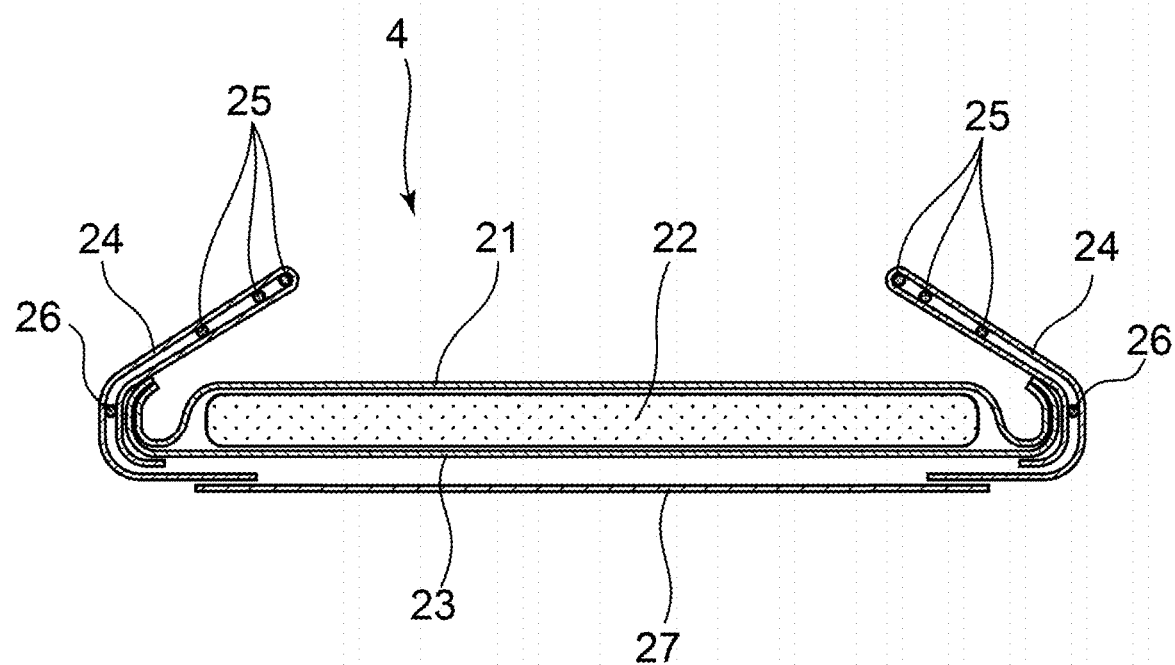
FIG. 3 is a cross-sectional view taken along line III-III of a crotch member illustrated in FIG. 2.

FIG. 3 is a schematic cross-sectional view taken along line III-III of the crotch member 4 illustrated in FIG. 2. As illustrated in FIG. 2 or 3, the crotch member 4 includes a top sheet 21, an absorbent body 22, a back sheet 23, left and right gathered sheets 24 and 24, a three-dimensional gathered elastic body 25, a crotch elastic body 26, and a cover sheet 27. The top sheet 21 is formed of a liquid permeable material such as a nonwoven fabric and is positioned on the wearer's skin side and covers the entire top surface of the absorbent body 22 so as to transmit urine, blood, or the like. The absorbent body 22 is formed by combining absorbent paper, cotton-like pulp, particulate or fibrous polymeric absorbent, or the like, and absorbs urine, blood, or the like, that have permeated through the top sheet 21, so as to be held inside the absorbent body 22. The absorbent body 22 has an hourglass shape, and a dorsal wide portion of the absorbent body 22 has an area larger than a ventral wide portion. The shape and size of the absorbent body 22 are not limited to those described above and may be appropriately selected according to the size and shape of the disposable undergarment. The back sheet 23 is formed of a liquid impermeable material such as a polyethylene film and covers the entire lower surface of the absorbent body 22, and prevents wastes, blood, or the like, from leaking to the outside.

The left and right gathered sheets 24 and 24 are formed of a nonwoven fabric, a material obtained by bonding a polyethylene film, or the like, onto a nonwoven fabric, and both open end portions of the folded sheet are joined to the left and right sides of the back sheet 23. The three-dimensional gathered elastic body 25 is joined to the inside of the folded back portion of the gathered sheets 24 and 24 in a state of being expanded in the longitudinal direction of the crotch member 4. This configuration forms three-dimensional gathers on the left and right sides of the crotch member 4, leading to prevention of leakage of wastes, or the like, from the crotch member 4. While the present embodiment is an exemplary case of providing three three-dimensional gathered elastic bodies 25 on each of the left and right sides, the number is not limited thereto.

The crotch elastic bodies 26 and 26 are joined to the base positions where the left and right gathered sheets 24 and 24 stand, in a state of being expanded in the longitudinal direction of the crotch member 4. The crotch elastic bodies 26 and 26 are arranged in the vicinity of both left and right ends of the absorbent body 22. When the weight of the interior of the crotch member 4 increases due to wastes, the left and right end portions of the crotch member 4 are pulled up by the tension of the crotch elastic bodies 26 and 26 so as to prevent a generation of a gap between the crotch member 4 and the wearer. Furthermore, since the crotch elastic bodies 26 and 26 are localized along the groin of the wearer, the crotch member 4 can be brought into close contact with the crotch of the wearer, leading to achievement of good fitness and leak-proofness. Note that while the crotch elastic body 26 according to the present embodiment is arranged one by one linearly along the left and right ends of the crotch member 4, it is not limited to this, but a plurality of crotch elastic bodies may be arranged, or may be arranged in a curved line.

Similarly to the elastic bodies 12, 13, 14, and 15, the three-dimensional gathered elastic body 25 and the crotch elastic body 26 are formed of stretchable thread-like materials such as natural rubber, polyurethane resin, and stretchable hot melt. Moreover, the elastic bodies 25 and 26 are not limited to thread-like elastic bodies, but may be band-like elastic bodies or sheet-like elastic bodies. Moreover, the entire gathered sheet 24 may be formed of a material such as a stretchable sheet. In the case of using a sheet-like elastic body or forming the entire gathered sheet 24 as a whole of a material such as a stretchable sheet, processing is performed so as to allow a desired tension to act at a position or in a direction which each of the elastic bodies 25 and 26 is extending, illustrated in FIGS. 2 and 3.

The cover sheet 27 is arranged in the outermost layer of the crotch member 4 and covers a boundary of each of the joint between the back sheet 23 and each of the left and right gathered sheets 24 and 24. A material such as a nonwoven fabric same as the material of the outer sheet of the ventral member 2 and the dorsal member 3 or the gathered sheet 24 may be used for the outside (clothing side of the wearer) of the cover sheet 27. The use of the same nonwoven fabric makes it possible to unify the appearance and texture of the entire disposable undergarment 1. Note that the back sheet 23 may be arranged on the outermost layer of the crotch member 4 without providing the cover sheet 27. Moreover, the cover sheet 27 and the gathered sheet 24 may be formed as an integral sheet.

Figure 4:
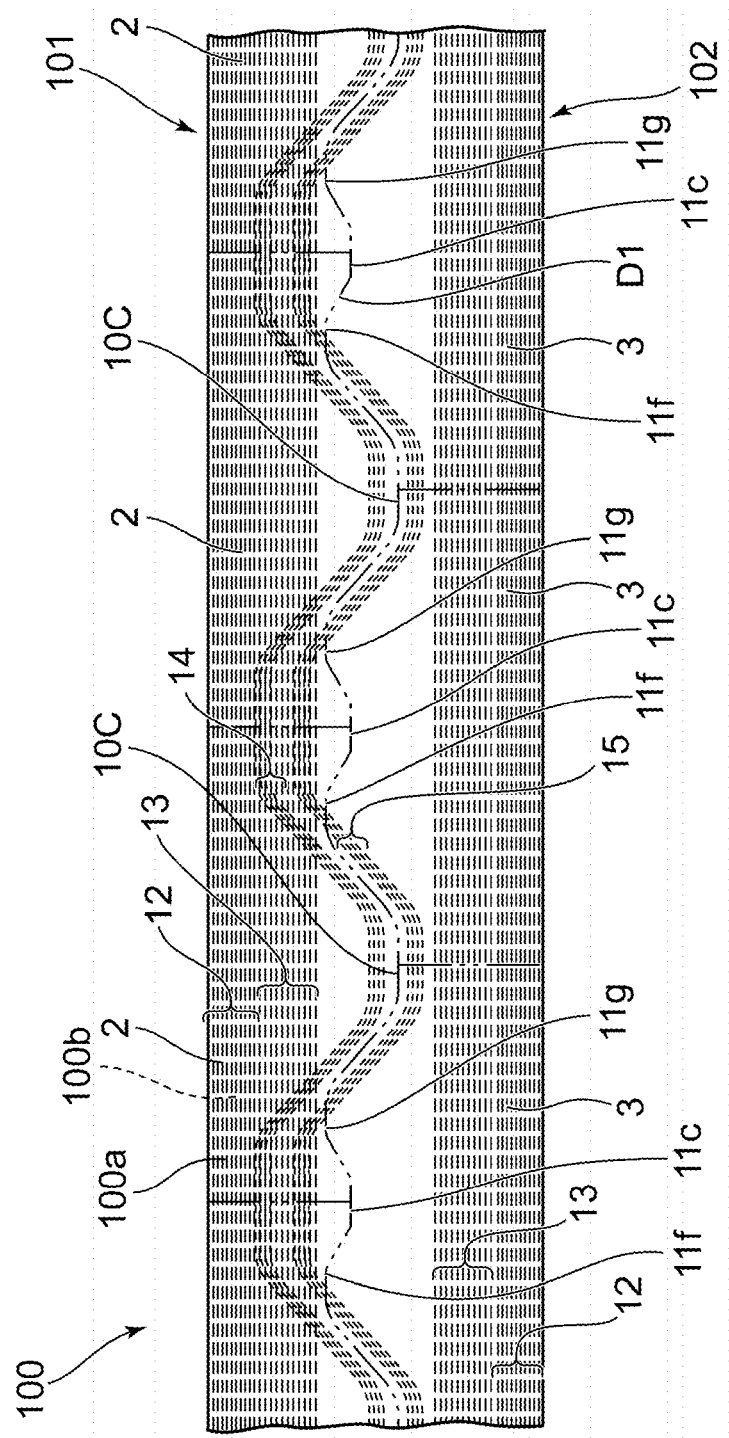
FIG. 4 is a plan view illustrating a portion of a laminated web for manufacturing the disposable undergarment illustrated in FIG. 1.
Figure 5:
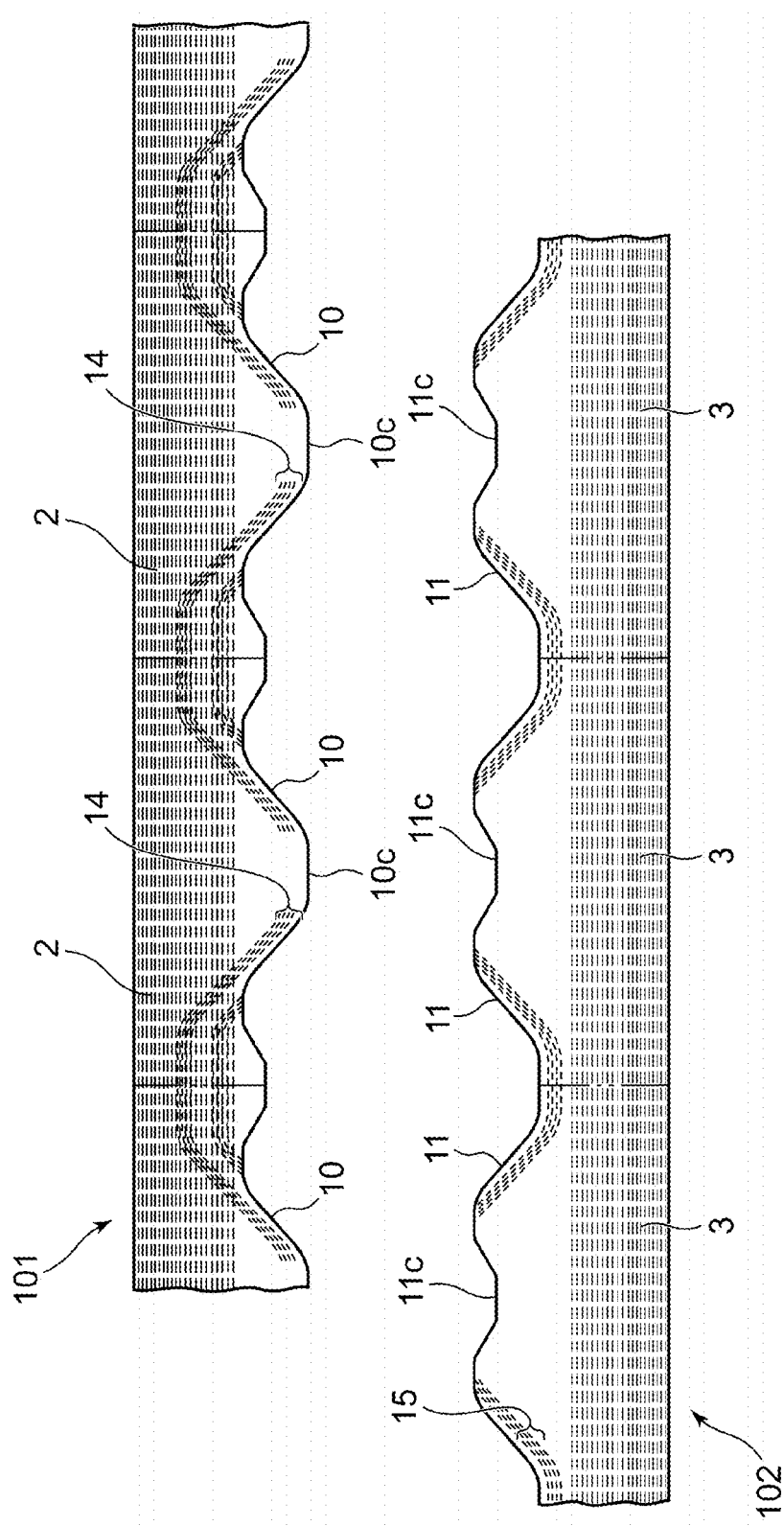
FIG. 5 is a plan view illustrating a state where two half-webs formed by cutting the laminated web are arranged by being spaced apart in a web width direction and shifted by half cycle in a web flow direction.
Figure 6:
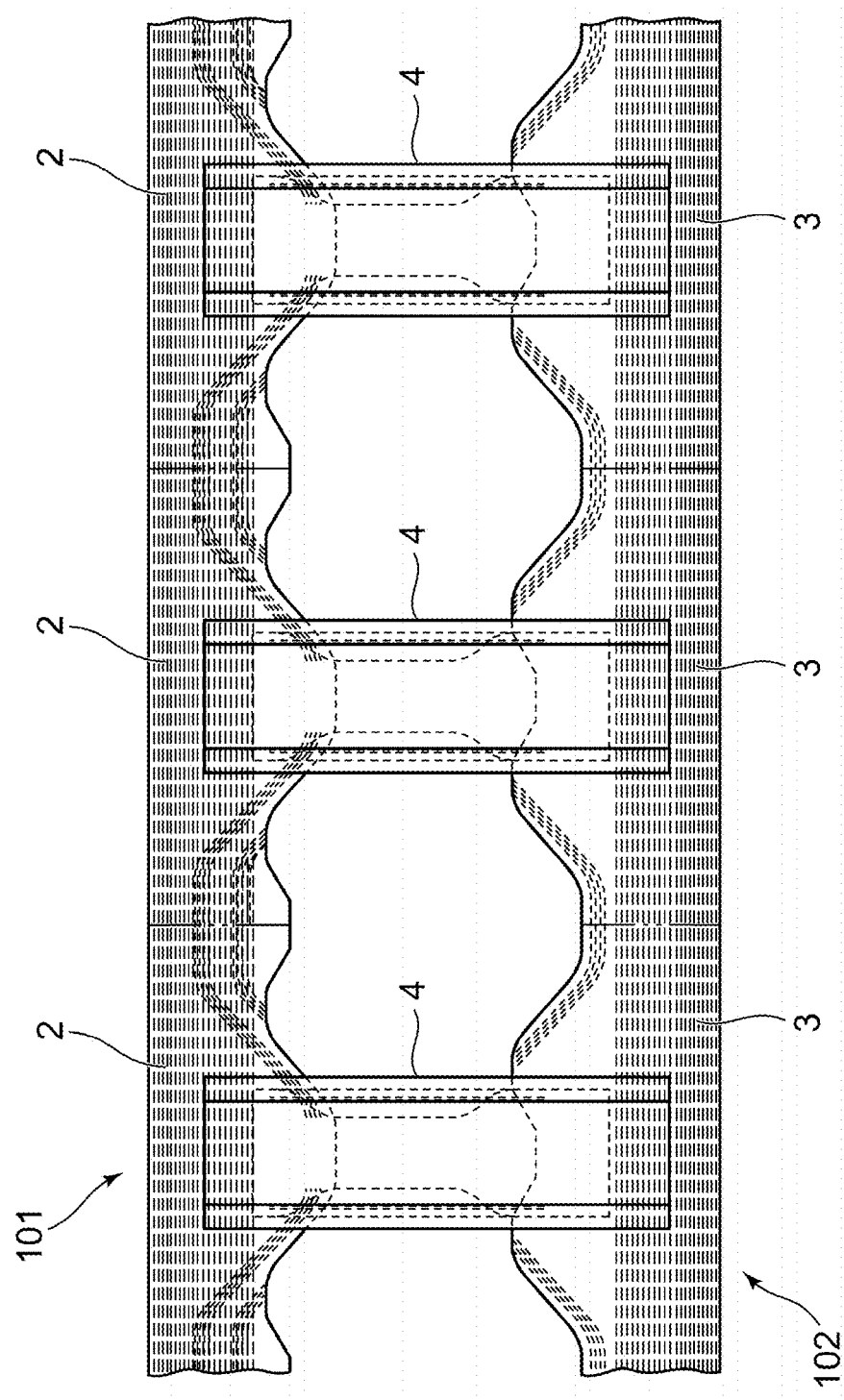
FIG. 6 is a plan view illustrating a state where a crotch member is joined to two half-webs.
Figure 7:
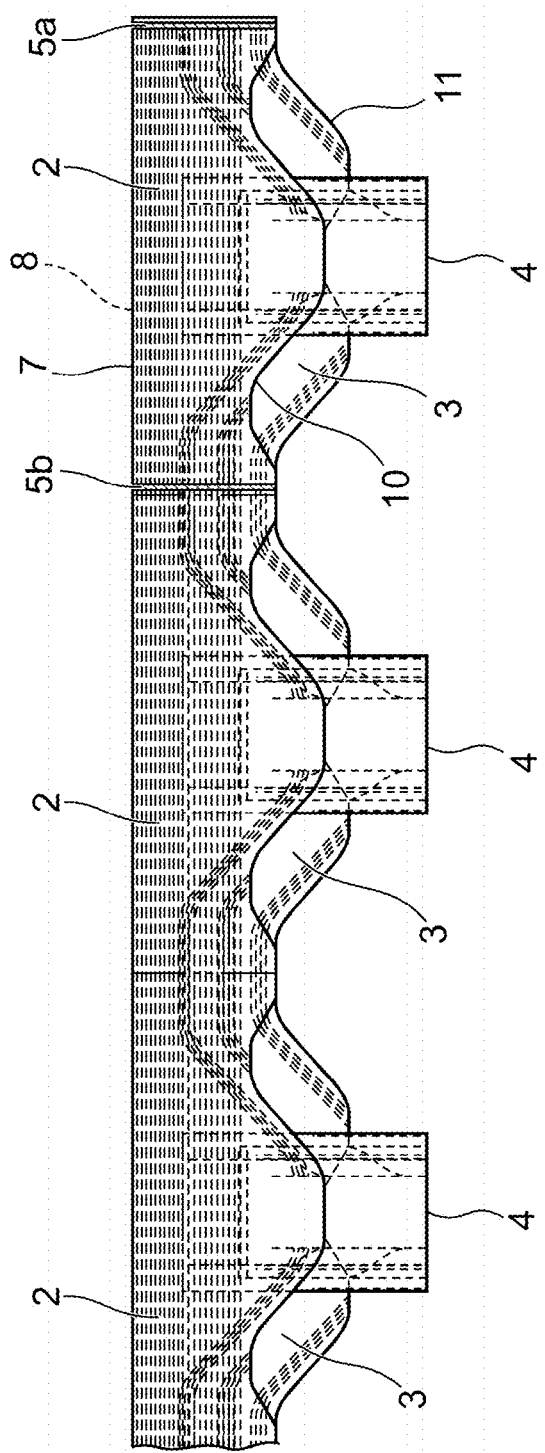
FIG. 7 is a plan view illustrating a state where the crotch member is folded to allow two half-webs to be overlaid with each other and joined in every cycle.

Next, a method for manufacturing the disposable undergarment 1 according to the present embodiment will be described with reference to the drawings. FIG. 4 is a plan view illustrating a portion of the laminated web for manufacturing the disposable undergarment 1. FIG. 5 is a plan view illustrating a state where two half-webs formed by cutting the laminated web are arranged by being spaced apart in a web width direction and shifted by half cycle in a web flow direction. FIG. 6 is a plan view illustrating a state where a crotch member is joined to two half-webs. FIG. 7 is a plan view illustrating a state where the crotch member is folded to allow two half-webs to be stacked with each other and joined in every cycle. For convenience of explanation, FIG. 7 illustrates an inverted version of a state of a half-web 102 overlaid on a half-web 101 illustrated in FIG. 6, that is, a state of the half-web 101 overlaid on the half-web 102. In each of the figures, the longitudinal direction of the web is the web flow direction and the direction orthogonal to the web flow direction is the web width direction. In each of the figures, the web, the ventral member, the dorsal member, and the crotch member are illustrated in expanded states without contraction of the elastic body.

First, as illustrated in FIG. 4, the elastic bodies 12, 13, 14, and 15 are sandwiched between an inner web 100a forming the inner sheet of each of the ventral member 2 and the dorsal member 3, and an outer web 100*b* forming the outer sheet of each of the ventral member 2 and the dorsal member 3, and in this state, the inner web 100*a* and the outer web 100*b* are overlaid and joined with each other, thereby forming a laminated web 100. At this time, an adhesive may be applied to the surface of each of the elastic bodies 12, 13, 14, and 15, or an adhesive may be applied to one or both of the surfaces of the inner web 100*a* and the outer web 100*b*, to which individual elastic bodies are jointed. Moreover, each of the elastic bodies may be fixed to the inner web 100*a* and/or the outer web 100*b* by heat sealing, or the like. The elastic bodies 12 and 13 are joined to the inner web 100*a* or the outer web 100*b* in a state of being expanded with a desired tension in the web flow direction. Each of the elastic bodies 14 and 15 is arranged in an appropriate position and shape in relation to a cutting line D1 to be described below in a state of being expanded with a desired tension, and then joined to the inner web 100*a* or the outer web 100*b*. While each of the elastic bodies 12, 13, 14, and 15 is a group of thread-like elastic bodies, it is not limited thereto, and a band-like elastic body or a sheet-like elastic body may be used. Moreover, it is allowable to form a region that expands or contracts on the inner web and/or the outer web in advance by forming the inner web 100*a* and/or the outer web 100*b* with the stretchable sheet. In the case of using a sheet-like elastic body or forming the inner web 100*a* and/or the outer web 100*b* with a stretchable sheet, processing is performed so as to allow a desired tension to act in a direction similar to each of the elastic bodies 12, 13, 14, and 15.

The cutting line D1 is a line formed with cyclic continuation of the crotch side edge 10 of the ventral member 2 and is also a line formed with continuation of the crotch side edge 11 of the dorsal member 3 shifted by half cycle. By appropriately designing the shape of the cutting line D1, it is possible to reduce overlapping portions and non-functioning portions in the material at the time of manufacturing and to avoid deficient portions, and thus, to achieve appropriate shapes of both the ventral member 2 and the dorsal member 3 formed by the cutting on the cutting line D1. As illustrated in FIG. 4, the cutting line D1 has a meandering shape with respect to the web flow direction. In detail, the cutting line D1 is formed such that intermediate lines 11*c* and 10*c* substantially parallel to the web flow direction are alternately arranged across the center line (not illustrated) in the web width direction, and a hill portion having a top portion 11*f* or 11*g* is arranged between the intermediate lines 11*c* and 10*c* in the flow direction. The top portions 11*f* and 11*g* are located more toward the intermediate line 11*c* than the intermediate line 10*c*, and are mirror symmetrical about the intermediate line 11*c*. The intermediate line 10*c* or 11*c* is connected to the top portion 11*f* or 11*g* via an inclined portion. The inclined portion is linear, but may be gently curved. It is preferable that the boundary between the intermediate line 10*c* or 11*c* and the inclined portion and the boundary between the top portion 11*f* or 11*g* and the inclined portion is gently curved.

As illustrated in FIG. 4, the elastic bodies 14 and 15 are arranged in parallel to each other in a meandering shape with respect to the web flow direction. The elastic bodies 14 and 15 each includes a portion extending along the intermediate line 10*c* of the cutting line D1 across the intermediate line 10*c*, inclined portion extending along the inclined portions on both sides of the intermediate line 10*c* of the cutting line D1 and then extending away from the inclined portion to reach a region in which the elastic body 13 is arranged, and an intermediate portion interconnecting these inclined portions. The above-described individual portions of the elastic bodies 14 and 15 are substantially linear but may be gently curved. Moreover, it is preferable that the boundary portion between the individual portions of the elastic bodies 14 and 15 is gently curved. The intermediate portions of the elastic bodies 14 and 15 have a substantially linear shape parallel to the elastic bodies 12 and 13. This arrangement makes it possible to suppress generation of wrinkles by contraction of the laminated web 100 in the width direction due to the influence of the elastic bodies 14 and 15. The elastic body 15 intersects the cutting line D1 in the vicinity of the intermediate portion of the inclined portion and is cut along the cutting line D1. The meandering elastic body 15 is cut along the cutting line D1 in the vicinity of the intermediate portion of the inclined portion, making it possible to prevent the edges of the ventral member 2 and the dorsal member 3 from being rounded due to the influence of the elastic body. It is also allowable to cut not merely the elastic body 15 but also the elastic body 14 along the cutting line D1.

Although not illustrated in FIG. 4, processing for reducing the tension may be performed onto each of the elastic bodies 12, 13, 14, and/or 15 arranged in a region where the crotch member 4 of each of the ventral members 2 and the dorsal member 3 of the laminated web 100 is to be overlaid. With this processing, it is possible to prevent generation of wrinkles in the crotch member 4 overlaid and joined with the ventral member 2 and the dorsal member 3, due to the tension of the elastic body. As processing of reducing the tension of the elastic body, for example, it is possible to appropriately select, for example, finely dividing the elastic body with a large number of protrusions, a cutter blade or the like, heat sealing the elastic body, or the like. Note that FIG. 5 illustrates the continuous half-web 101 of the ventral member 2 in which processing of reducing the tension has been performed on the leg-fitting elastic body 14 arranged in the region along the intermediate line 10*c* of the crotch side edge 10 of the ventral member 2.

Next, the laminated web 100 is cut along the cutting line D1 continuous in the web flow direction by defining one of the crotch side edge 10 of the ventral member 2 and the crotch side edge 11 of the dorsal member 3 as one cycle. The line formed with cyclic continuation of the crotch side edge 10 of the ventral member 2 and the line formed with cyclic continuation of the crotch side edge 11 of the dorsal member 3 match with each other when they are overlaid with each other shifted by half cycle in the web flow direction. By cutting the laminated web 100 along the cutting line D1, the continuous half-web 101 of the ventral member 2 and a continuous half-web 102 of the dorsal member 3 are formed.

Next, as illustrated in FIG. 5, either the continuous half-web 101 of the ventral member 2 or the continuous half-web 102 of the dorsal member 3 is moved in the web width direction while being shifted by half cycle in the web flow direction, thereby allowing each of the ventral member 2 of the half-web 101 and the dorsal member 3 of the half-web 102 to be arranged to face each other and spaced apart from each other in every cycle. The interval between the half-web 101 and the half-web 102 is set to an appropriate interval needed for overlaying and joining each of the crotch member 4 with each of the ventral members 2 and each of the dorsal members 3. Note that shifting the half-web 101 or the half-web 102 by half cycle in the web flow direction may be performed after completing moving the half-webs in the web width direction, or shifting the half-webs by half cycle in the web flow direction may be performed while moving them in the web width direction.

As a method for shifting the half-web in the web flow direction by half cycle, it is possible to employ various methods such as changing the conveying distance and speed in the web flow direction of the half-web.

Next, as illustrated in FIG. 6, each of the crotch members 4 is overlaid and joined with the central portion of each of the ventral members 2 of the half-web 101 and the central portion of each of the ventral members 2 of the half-web 102. The crotch member 4 is joined to the ventral member 2 and the dorsal member 3 with an adhesive such as a hot melt. Although the left and right end portions of each of the ventral members 2 of the half-web 101 protrude toward the half-web 102, this would not generate wrinkles due to the tension of the elastic body because this protruding portion contains no elastic body.

Next, as illustrated in FIG. 7, the crotch member 4 is bent to overlay the half-web 101 and the half-web 102 such that the inner sheet of each of the ventral member 2 and the dorsal member 3 faces the inner side. No wrinkles are generated because no elastic body is contained in the protruding portions in the left and right end portions of each of the ventral members 2 of the half-web 101. When the half-web 101 and the half-web 102 are overlaid, this allows the left and right end portions of the ventral member 2 and each of the dorsal members 3 in each of the cycles to be overlaid with stabilized positions in the web width direction and in a state where generation of wrinkles and deviations is suppressed.

Next, the joints 5a and 5b are formed along the left and right end portions of the ventral member 2 and the dorsal member 3 overlaid by each of the cycles. The ventral member 2 and the dorsal member 3 are joined with each other by these joints 5a and 5b. The joints 5a and 5b are intermittently or continuously formed between the waist side edges 7 and 8 of the ventral member 2 and the dorsal member 3, and the crotch side edges 10 and 11. Since the left and right end lines 10a and 10b of the crotch side edge 10 of the ventral member 2 and the left and right end lines 11a and 11b of the crotch side edge 11 of the dorsal member 3 are substantially parallel to the waist side edges 7 and 8, respectively, it is possible to form the joints 5a and 5b with sufficient width and across a substantially entire length of the portion between the waist side edges 7 and 8 and the crotch side edges 10 and 11. The left and right joints 5a and 5b may be formed by an adhesive such as a hot melt adhesive or by various sealing methods such as heat sealing and ultrasonic sealing.

Next, the pant-type disposable undergarment 1 illustrated in FIG. 1 is manufactured in the same orientation continuously in the web flow direction by cutting at a portion between the adjacent joints 5a and 5b of the ventral member 2 and the dorsal member 3 joined in every cycle. With the processing described above according to the present embodiment, it is possible to provide a disposable undergarment that being less wasteful of materials, and having appropriate shapes in both the ventral and dorsal sides. Moreover, it is also possible to provide a method for continuously manufacturing such a disposable undergarment.

Second Embodiment

Figure 8:
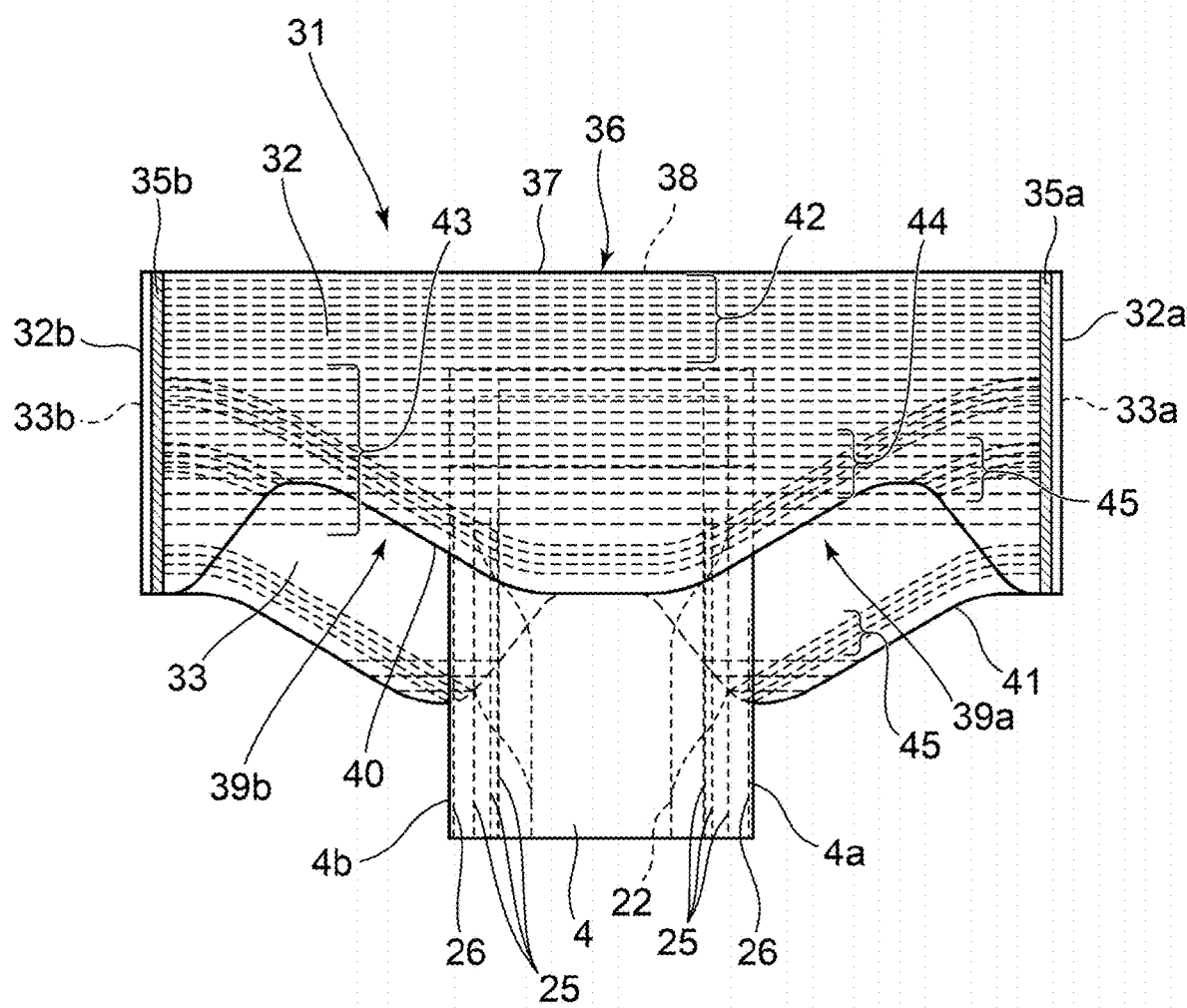
FIG. 8 is a front view of a disposable undergarment according to another embodiment of the present invention.
Figure 9:
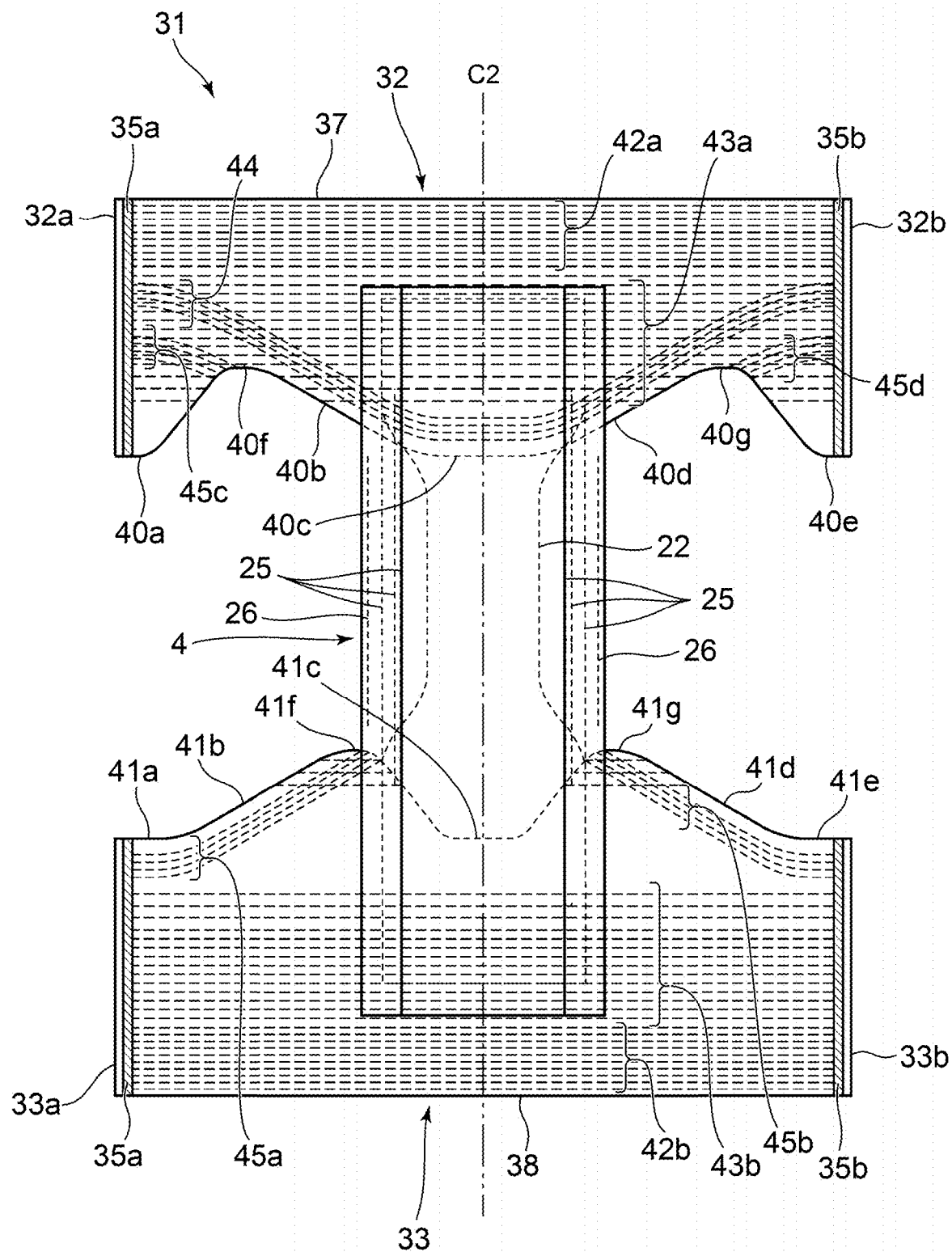
FIG. 9 is an exploded view of the disposable undergarment illustrated in FIG. 8.
Figure 10:
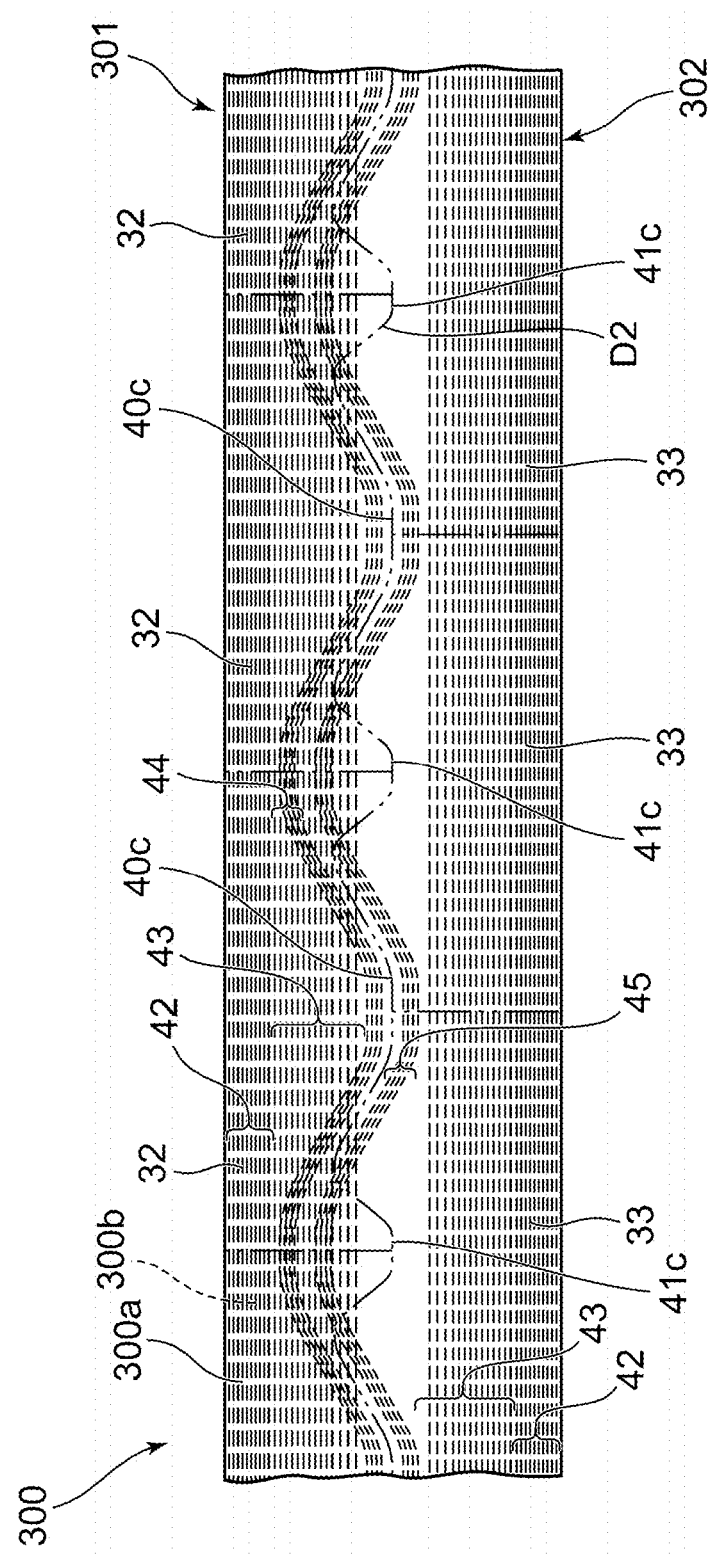
FIG. 10 is a plan view illustrating a portion of the laminated web for manufacturing the disposable undergarment illustrated in FIG. 8.

Next, a disposable undergarment according to another embodiment of the present invention will be described with reference to the drawings. FIG. 8 is a front view of a disposable undergarment 31 according to another embodiment. FIG. 9 is an exploded view of the disposable undergarment 31 illustrated in FIG. 8. FIG. 10 is a plan view illustrating a portion of a laminated web 300 for manufacturing the disposable undergarment 31 illustrated in FIG. 8. Individual members in these figures are illustrated in a state where the elastic bodies are expanded state without being contracted. Components of the disposable undergarment 31, having same structures and functions as those of the disposable undergarment 1 are denoted by the same names or reference numerals, and description thereof is omitted as appropriate.

As illustrated in FIGS. 8 and 9, the disposable undergarment 31 is a pant-type disposable diaper. The disposable undergarment 31 includes a ventral member 32 positioned on a front side of the wearer's torso, a dorsal member 33 positioned on a back side of the wearer's torso, and the crotch member 4 joined to a central portion on an inner surface side of the ventral member 32 and to a central portion of an inner surface side of the dorsal member 33 and located at the crotch of the wearer. As the crotch member 4, it is allowable to use the one same as the disposable undergarment 1. The ventral member 32 and the dorsal member 33 are formed by overlaying an inner sheet positioned on a skin side of the wearer and an outer sheet positioned on a clothing side of the wearer and sandwiching waist-fitting elastic bodies 42, a body-fitting elastic body 43, and leg-fitting elastic bodies 44 and 45, between the sheets, and by joining the sheets in this state. The materials of the inner sheet and the outer sheet of the ventral member 32 and the dorsal member 33 may be the same as the materials of the inner sheet and the outer sheet of the ventral member 2 and the dorsal member 3.

The disposable undergarment 31 is formed into a pant-type diaper by folding the crotch member 4 joined to the ventral member 32 and the dorsal member 33 and then, by joining the left and right end portions in a state where the ventral member 32 and the dorsal member 33 are overlaid with each other. A left joint 35a is formed along left end portions 32a and 33a of the ventral member 32 and the dorsal member 33, respectively, and a right joint 35b is formed along right end portions 32b and 33b of the ventral member 32 and the dorsal member 33, respectively. The left and right joints 35a and 35b may be formed with various sealing methods similar to the case of the left and right joints 5a and 5b of the disposable undergarment 1.

A waist opening 36 of the disposable undergarment 1 is formed by being encircled by a waist side edge 37 at an upper end of the ventral member 32 and by a waist side edge 38 at an upper end of the dorsal member 33. The left leg opening 39a is formed by being encircled by a crotch side edge 40 at a lower end of the ventral member 32, a crotch side edge 41 at a lower end of the dorsal member 33, and the left side edge 4a of the crotch member 4. The right leg opening 39b is formed by being encircled by the crotch side edge 40 of the ventral member 32, the crotch end edge 41 of the dorsal member 33, and the right side edge 4b of the crotch member 4.

As illustrated in FIG. 8 or 9, in a state where the ventral member 32 and the dorsal member 33 are expanded, the waist side edge 37 of the ventral member 32 and the waist side edge 38 of the dorsal member 33 have linear shapes and an equal length. The left and right end portions 32a and 32b of the ventral member 32 have linear shapes perpendicular to the waist side edge 37. The left and right end portions 33a and 33b of the dorsal member 33 have linear shapes perpendicular to the waist side edge 38. The lengths of the left and right end portions 32a and 32b of the ventral member 32 are equal to the lengths of the left and right end portions 33a and 33b of the dorsal member 33, respectively. Each of the crotch side edge 40 of the ventral member 32 and the crotch side edge 41 of the dorsal member 33 has a symmetrical shape about a center line C2 having a common left-right widths on the ventral member 32 and the dorsal member 33.

As illustrated in FIG. 9, in a state where the ventral member 32 and the dorsal member 33 are separated and expanded, that is, in a state where the disposable undergarment 31 is developed, a left half and a right half of the crotch side edge 40 of the ventral member 32 are symmetrical about the center line C2. The crotch side edge 40 includes a left end line 40a, a left recessed line 40b, an intermediate line 40c, a right recessed line 40d, and a right end line 40e. The left end line 40a, the intermediate line 40c, and the right end line 40e have linear shapes substantially parallel to the waist side edge 7. The intermediate line 40c is bisected by the center line C2. The left recessed line 40b is connected to the left end line 40a and the intermediate line 40c. The left recessed line 40b has a shape recessed in a direction toward the waist side edge 37. A bottom portion 40f of the left recessed line 40b is a portion closest to the waist side edge 37 and is located more toward the left end portion 32a than the center line C2 of the ventral member 32. The right recessed line 40d is connected to the right end line 40e and the intermediate line 40c. The right recessed line 40d has a shape recessed in a direction toward the waist side edge 37. A bottom portion 40g of the right recessed line 40d is a portion closest to the waist side edge 37 and is located more toward the right end portion 32b than the center line C2 of the ventral member 32.

As illustrated in FIG. 9, the left half and the right half of the crotch side edge 41 of the dorsal member 33 are symmetrical about the center line C2. The crotch side edge 41 includes a left end line 41a, a left protruding line 41b, an intermediate line 41c, a right protruding line 41d, and a right end line 41e. The left end line 41a, the intermediate line 41c, and the right end line 41e have a linear shape substantially parallel to the waist side edge 38. The intermediate line 41c is bisected by the center line C2. The left protruding line 41b is connected to the left end line 41a and the intermediate line 41c. The left protruding line 41b has a shape protruding in a direction away from the waist side edge 38. A top portion 41f of the left protruding line 41b is a portion farthest away from the waist side edge 38 and is located more toward the center line C2 than the left end portion 33a of the dorsal member 33. The right protruding line 41d is connected to the right end line 41e and the intermediate line 41c. The right protruding line 41d has a shape protruding in a direction away from the waist side edge 38. A top portion 41g of the right protruding line 41d is the portion farthest away from the waist side edge 38 and is located more toward to the center line C2 than the right end portion 33b of the dorsal member 33.

As illustrated in FIG. 9, the shape of a left half of the crotch side edge 40 bisected at the center line C2 of the ventral member 32 is the same as the shape of the right half of the crotch side edge 41 bisected at the center line C2 of the dorsal member 33. The shapes of the left end line 40a, the left protruding line 40b, the bottom portion 40f, and the left half of the intermediate line 40c of the crotch side edge 40 are the same as the shapes of the right half of the intermediate line 41c, the right protruding line 41d, the top portion 41g, and the right end line 41e of the crotch side edge 41, respectively. In short, when the left half of the crotch side edge 40 of the ventral member 32 is moved in the left-right direction and in an approaching direction to abut against the right half of the crotch side edge 41 of the dorsal member 33, the shapes of both portions match.

As illustrated in FIG. 9, the shape of a right half of the crotch side edge 40 bisected at the center line C2 of the ventral member 32 is the same as the shape of the left half of the crotch side edge 41 bisected at the center line C2 of the dorsal member 33. The shapes of the right end line 40e, the right protruding line 40d, the bottom portion 40g, and the right half of the intermediate line 40c of the crotch side edge 40 are the same as the shapes of the left half of the intermediate line 41c, the left protruding line 41b, the top portion 41f, and the left end line 41a of the crotch side edge 41, respectively. In short, when the right half of the crotch side edge 40 of the ventral member 32 is moved in the left-right direction and in an approaching direction to abut against the left half of the crotch side edge 41 of the dorsal member 33, the shapes of both portions match.

In the disposable undergarment 1, the distance between the waist side edge 7 and the crotch side edge 8 of the ventral member 2 is longer at a position of the center line C1 of the ventral member 2 than at the position of the left and right end portions 2a and 2b of the ventral member 2. In contrast, in the disposable undergarment 31, the distance between the waist side edge 37 and the crotch side edge 38 of the ventral member 32 is equal at positions of the left and right end portions 32a and 32b of the ventral member 32 and at a position of the center line C2 of the ventral member 32.

In the ventral member 32 of the disposable undergarment 31, the left and right bottom portions 40f and 40g having the shortest distance between the waist side edge 37 and the crotch side edge 40 are located at positions more toward the left and right end portions 32a and 32b, respectively, than the center line C2 of the ventral member 32. This configuration makes it possible to increase the left-right width of a downward protrusion between the left and right bottom portions 40f and 40g of the ventral member 32, leading to an increase in the left-right width of a region to cover the wearer's groin and periphery thereof on the ventral member 32. In this manner, the disposable undergarment 31 can form the ventral member 32 into an appropriate shape.

The dorsal member 33 of the disposable undergarment 31 is configured such that the left and right protruding lines 41b and 41d continuous respectively to the left and right end lines 41a and 41e protrude in a direction away from the waist side edge 38, making it possible to increase the left-right width of the downward protrusion of the dorsal member 33. Moreover, in the dorsal member 33, the top portions 41f and 41g having the longest distance between the waist side edge 38 and the crotch side edge 41 are respectively located more toward the center line C2 than the left and right end portions 33a and 33b of the dorsal member 33. This configuration makes it possible to locate the top portions 41f and 41g of the downward protrusion of the dorsal member 33 near the central portion of the dorsal member 33 to which the crotch member 4 has been joined. The recessed shape of the intermediate line 41c of the dorsal member 33 would be no problem since the central portion of the dorsal member 33 is covered with the crotch member 4. In this manner, in the disposable undergarment 31, it is possible to realize an appropriate shape of the dorsal member 33 with the sufficiently increased left-right width and the top-bottom length of the portion to cover the buttock of the wearer.

Furthermore, in the disposable undergarment 31, the distance between the waist side edge 37 and the crotch side edge 40 become longest at the left and right end portions 32a, 32b, 33a, and 33b. This makes it possible to realize a shape like a trunks type with longer joints.

As illustrated in FIGS. 8 and 9, the ventral member 32 and the dorsal member 33 include waist-fitting elastic bodies 42a and 42b that stretch and contract in the left-right direction, and body-fitting elastic bodies 43a and 43b, respectively. Moreover, the ventral member 32 includes a leg-fitting elastic body 44 and a portion of a leg-fitting elastic body 45. The dorsal member 33 includes a portion of the leg-fitting elastic body 45.

The waist-fitting elastic body 42a is arranged over substantially the entire region from the left end portion 32a to the right end portion 32b in the waist side edge 37 and adjacent regions of the ventral member 32, and is joined in an expanded state, to the ventral member 32. The waist-fitting elastic body 42b is arranged over substantially the entire region from the left end portion 33a to the right end portion 33b in the waist side edge 38 and adjacent regions of the dorsal member 33, and is joined in an expanded state, to the dorsal member 33. Although not illustrated, waist gathers are formed in a region of the ventral member 32 and the dorsal member 33 where the waist-fitting elastic bodies 42a and 42b are joined.

The body-fitting elastic body 43a is arranged over substantially the entire area from the left end portion 32a to the right end portion 32b in the adjacent region on the crotch side edge 40 side from the region where the waist-fitting elastic body 42a of the ventral member 32 is joined, and is joined in an expanded state, to the ventral member 32. The body-fitting elastic body 13a of the disposable undergarment 1 is arranged above the crotch side edge 10 of the ventral member 2 and does not intersect the crotch side edge 10. In contrast, the body-fitting elastic body 43a of the disposable undergarment 31 is arranged between the left recessed line 40b and the right recessed line 40d, between the left recessed line 40b and the left end portion 32a of the ventral member 32, and between the right recessed line 40d and the right end portion 32b of the ventral member 32. The body-fitting elastic body 43a is not arranged in the neighborhood of the left end line 40a, the intermediate line 40c, or the right end line 40e of the crotch side edge 40 of the ventral member 32.

The body-fitting elastic body 43b is arranged over substantially the entire area from the left end portion 33a to the right end portion 33b in the adjacent region on the crotch side edge 41 side from the region where the waist-fitting elastic body 42b of the dorsal member 33 is joined, and is joined in an expanded state, to the dorsal member 33. Although not illustrated, body-fitting gathers are formed in a region of the ventral member 32 and the dorsal member 33 where the body-fitting elastic bodies 43a and 43b are joined.

The leg-fitting elastic body 44 is arranged in a meandering manner so as to extend along the intermediate line 40c and the left and right recessed lines 40b and 40d of the crotch side edge 40 of the ventral member 32, rise diagonally away from the crotch side edge 40 from the neighborhood of the bottom portions 40f and 40g, and extend to the left and right end portions 32a and 32b of the ventral member 32 along the upper portion in the region of the body-fitting elastic body 43a, and is joined in an expanded state, to the ventral member 32. The leg-fitting elastic body 45 includes: a portion 45a extending along the left end line 41a and the left protruding line 41b of the crotch side edge 41 of the dorsal member 33 and intersecting the top portion 41f; a portion 45b extending along the right end line 41e and the right protruding line 41d of the crotch side edge 41 of the dorsal member 33 and intersecting the top portion 41g; and left and right portions 45c and 45d extending being spaced apart in parallel with each other below the leg-fitting elastic body 44 in the ventral member 32.

Although not illustrated, leg gathers are formed in a region where the leg-fitting elastic bodies 44 or 45 are joined around the crotch side edge 40 of the ventral member 32 and around the crotch side edge 41 of the dorsal member 33.

Each of the waist-fitting elastic body 42, the body-fitting elastic body 43, and the leg-fitting elastic bodies 44 and 45 is formed with a group of a plurality of thread-like elastic bodies. Each of the thread-like elastic bodies is formed of a stretchable material such as natural rubber, polyurethane resin, and stretchable hot melt. The elastic bodies 42, 43, 44, and 45 are not limited to thread-like elastic bodies, but may be band-like elastic bodies or sheet-like elastic bodies. Furthermore, the entire ventral member 32 and/or the dorsal member 33 may be formed of a material such as a stretchable sheet. In the case of using a sheet-like elastic body or forming the entire ventral member 32 and/or the dorsal member 33 as a whole of a material such as a stretchable sheet, processing is performed so as to allow a desired tension to act in a direction similar to each of the elastic bodies 42, 43, 44, and 45.

In FIG. 9, each of the elastic bodies 42, 43, 44, and/or 45 arranged in a region of the ventral member 32 and the dorsal member 33 overlaid with the crotch member 4 may be processed to reduce the tension of the elastic body. This processing results in suppression of deformation or contraction of the crotch member 4 by the tension of the elastic body. As processing of reducing the tension of the elastic body, for example, it is possible to appropriately select, for example, finely dividing the elastic body with a large number of protrusions, a cutter blade or the like, finely heat sealing the elastic body, or the like.

As illustrated in FIG. 9, as the crotch member 4, it is allowable to use the one same as the crotch member 4 of the disposable undergarment 1. The shape of the crotch member 4 and the position and the size of the portion where the crotch member 4 is overlaid with and joined to the ventral member 32 or the dorsal member 33 are not limited to those described above and may be appropriately changed in accordance with the size and shape of the disposable diaper 31.

The disposable diaper 31 can be manufactured by a similar manufacturing method as the method for the disposable diaper 1 using a laminated web 300. First, as illustrated in FIG. 10, the elastic bodies 42, 43, 44, and 45 are sandwiched between an inner web 300a forming the inner sheet of each of the ventral member 32 and the dorsal member 33, and an outer web 300b forming the outer sheet of each of the ventral member 32 and the dorsal member 33, and in this state, the inner web 300a and the outer web 300b are overlaid and joined with each other, thereby forming the laminated web 300. Each of the elastic bodies 42, 43, 44, and 45 is arranged in an appropriate position and shape in relation to a cutting line D2 in a state of being expanded with a desired tension, and then joined to the inner web 300a or the outer web 300b. The elastic bodies 42, 43, 44, and 45 are not limited to thread-like elastic bodies, but may be band-like elastic bodies or sheet-like elastic bodies. The inner web 300a and/or the outer web 300b may be formed with a stretchable sheet. In the case of using a sheet-like elastic body or forming the inner web 300a and/or the outer web 300b with a stretchable sheet, processing is performed so as to allow a desired tension to act in a direction similar to each of the elastic bodies 42, 43, 44, and 45. As illustrated in FIG. 10, while in the present embodiment, the elastic bodies 44 and 45 are arranged in a meandering shape with respect to the web flow direction, there are few linear portions parallel to the web flow direction in comparison with the elastic bodies 14 and 15 of the previous embodiment, leading to an entire arrangement with gently curved shapes.

The present invention is not limited to the above-described embodiments and modified examples. For example, the disposable undergarment according to the present invention may be a pad holder that does not include an absorbent body inside the crotch member and configured to be used by attaching an absorbent pad including an absorbent body.

It should be understood that the invention is not limited to the above-described embodiment, but may be modified into various forms on the basis of the spirit of the invention. Additionally, the modifications are included in the scope of the invention.

What is claimed is:

1. A disposable undergarment comprising:
    a ventral member;
    a dorsal member including left and right end portions respectively joined to left and right end portions of the ventral member; and
    a crotch member joined to both central portions of the ventral member and the dorsal member,
    wherein each of the ventral member and the dorsal member includes an elastic body that expands and contracts at least in a left-right direction, and
    in a state where the ventral member and the dorsal member are separated from each other and expanded,
    a left half of a crotch side edge between a left side end of the ventral member and a center of the ventral member has a first shape, a right half of a crotch side edge between a center of the dorsal member and a right side end of the dorsal member has a second shape, wherein the first shape and the second shape match,
    a right half of the crotch side edge between the center of the ventral member and a right side end of the ventral member has a third shape, a left half of the crotch side edge between a left side end of the dorsal member and the center of the dorsal member has a fourth shape, wherein the third shape and the fourth shape match,
    the left half and the right half of the crotch side edge of the ventral member are symmetrical about a center line of the ventral member,
    the left half and the right half of the crotch side edge of the ventral member respectively include a left recessed line and a right recessed line recessed in a direction toward the waist side edge of the ventral member, between the center line of the ventral member and the left and right end portions,
    each of the left recessed line and the right recessed line is formed to have a bottom portion closest to the waist side edge of the ventral member, being located at a position excluding the center line and the left and right end portions, located at a position more toward the left and right end portions than the center line,
    the left half and the right half of the crotch side edge of the dorsal member are symmetrical about a center line of the dorsal member,
    the left half and the right half of the crotch side edge of the dorsal member respectively include a left protruding line and a right protruding line protruding in a direction away from the waist side edge of the dorsal member, between the center line of the dorsal member and the left and right end portions, and
    each of the left protruding line and the right protruding line is formed to have a top portion farthest away from the waist side edge of the dorsal member, being located at a position excluding the center line and the left and right end portions, located at a position more toward the center line than the left and right end portions.

2. The disposable undergarment according to claim 1, wherein a distance between the waist side edge and the crotch side edge of the ventral member is longer at a position of the center line of the ventral member than at positions of the left and right end portions of the ventral member.

3. The disposable undergarment according to claim 1, wherein a distance between the waist side edge and the crotch side edge of the ventral member is equal at a position of the center line of the ventral member and at positions of the left and right end portions of the ventral member.

4. The disposable undergarment according to claim 1, wherein the crotch member overlaps with at least a portion of portions farthest away from the waist side edge of the left and right protruding lines of the crotch side edge of the dorsal member.

5. A method for manufacturing the disposable undergarment according to claim 1, the method comprising:
    forming a laminated web by joining an inner web and an outer web with an elastic body to be expanded at least in a web flow direction sandwiched between the inner web and the outer web;
    cutting the laminated web along a continuous cutting line in the web flow direction with the crotch side edge of one of the ventral member and the dorsal member of the disposable undergarment as one cycle so as to divide the laminated web into a half-web formed of continuous ventral member and a half-web formed of continuous dorsal member;
    moving one of the half-web formed of continuous ventral member and the half-web formed of continuous dorsal member in a web width direction while shifting the half-webs by half cycle in the web flow direction so as to allow the ventral member and the dorsal member in every cycle to be spaced from each other and to face each other;
    joining each of the crotch members to the ventral member and the dorsal member in every cycle of the both half-webs;
    overlaying both the webs with each other in a state where each of the crotch members is folded;
    joining the ventral member and the dorsal member in each of the cycles with each other at each of the left and right end portions; and
    forming the disposable undergarment by cutting the joined ventral member and the dorsal member in every cycle.

* * * * *